(12) United States Patent
Van Leest

(10) Patent No.: US 9,241,674 B2
(45) Date of Patent: Jan. 26, 2016

(54) DISTORTION REDUCED SIGNAL DETECTION

(75) Inventor: Adriaan Johan Van Leest, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/239,798

(22) PCT Filed: Sep. 12, 2012

(86) PCT No.: PCT/IB2012/054734
§ 371 (c)(1),
(2), (4) Date: Feb. 20, 2014

(87) PCT Pub. No.: WO2013/046082
PCT Pub. Date: Apr. 4, 2013

(65) Prior Publication Data
US 2014/0213861 A1 Jul. 31, 2014

Related U.S. Application Data

(60) Provisional application No. 61/540,596, filed on Sep. 29, 2011.

(51) Int. Cl.
*G06K 9/00* (2006.01)
*A61B 5/00* (2006.01)
(Continued)

(52) U.S. Cl.
CPC ............ *A61B 5/7235* (2013.01); *A61B 5/0075* (2013.01); *A61B 5/02416* (2013.01); *A61B 5/14551* (2013.01); *G06K 9/2018* (2013.01); *G06K 9/624* (2013.01)

(58) Field of Classification Search
None
See application file for complete search history.

(56) References Cited

U.S. PATENT DOCUMENTS

2003/0088164 A1  5/2003  Stetson
2010/0142805 A1  6/2010  Maxwell et al.

FOREIGN PATENT DOCUMENTS

WO  2010100594 A2  9/2010
WO  2011021128 A2  2/2011
(Continued)

OTHER PUBLICATIONS

Verkruysse et al, "Remote Plethysmographic Imaging Using Ambient Light" Optics Express, Optical Society of America, vol. 16, No. 26, 2008, pp. 21434-21445.
(Continued)

*Primary Examiner* — Siamak Harandi

(57) ABSTRACT

The present invention relates to a device and a method for extracting information from detected characteristic signals. A data stream (26) derivable from electromagnetic radiation (14) emitted or reflected by an object (12) is received. The data stream (26) comprises a continuous or discrete time-based characteristic signal ( ; 98) comprising at least two main components (92a, 92b, 92c) related to respective complementary channels (90a, 90b, 90c) of a signal space (88). The characteristic signal ( ; 98) is mapped to a defined component representation ( , , , ; , ) under consideration of a substantially linear algebraic signal composition model so as to specify a linear algebraic equation. The linear algebraic equation is at least partially solved under consideration of an at least approximate estimation of specified signal portions ( , , ). Consequently, an expression highly indicative of the at least one at least partially periodic vital signal (20) can be derived from the linear algebraic equation.

15 Claims, 4 Drawing Sheets

(51) Int. Cl.
*G06K 9/20* (2006.01)
*G06K 9/62* (2006.01)
*A61B 5/024* (2006.01)
*A61B 5/1455* (2006.01)

(56) References Cited

FOREIGN PATENT DOCUMENTS

| WO | 2011042839 A1 | 4/2011 |
| WO | 2011042858 A1 | 4/2011 |
| WO | 2012093358 A1 | 7/2012 |

OTHER PUBLICATIONS

Sahindrakar, "Improving Motion Robustness of Contact-Less Monitoring of Heart Rate Using Video Analysis", University of Technology, Eindhoven, NL Aug. 24, 2011 Retrieved From the Internet: URL:http://alexandria.tue.nl/extra1/afstversl/wsk-i/sahindrakar2011.pdf, 58 Pages.

Poh et al, "Non-Contact, Automated Cardiac Pulse Measurments Using Video Imaging and Blind Source Separation", Optics Express, vol. 18, No. 10, May 2010, p. 10762.

Verkruijsse et al, "A Novel Biometric Signature: Multi-Site, Remote (>100M) Photo-Plethysmography Using Ambient Light" Technical Note PR-TN 2010/00097, Mar. 1, 2010.

Cennini et al, "Heart Rate Monitoring Via Remote Photoplethysmography With Motion Artifacts Reduction", Optics Express, vol. 18, No. 5, Mar. 1, 2010, p. 4867.

Klinker et al: "The Measurement of Highlights in Color Images"; International Journal of Computer Vision, vol. 2, pp. 7-32, 1988.

Shafer: "Using Color to Separate Reflection Components"; Technical Report 136, University of Rochester, April 1984, 31 page Document.

Storring et al: "Estimation of the Illuminant Colour Using Highlights From Human Skin"; International Conference on Color in Graphics and Image Processing, 2000, 6 page Document.

Takano et al: "Heart Rate Measurement Based on a Time-Lapse Image": Medical Engineering & Physics, Vol. 29, (2007), pp. 853-857.

Tominaga: "Dichromatic Reflection Models for a Variety of Materials"; Color Research and Application, 19:277-285, 1994.

DISTORTION REDUCED SIGNAL DETECTION

FIELD OF THE INVENTION

The present invention relates to a device and method for extracting information from characteristic signals, wherein the characteristic signals are embedded in a data stream derivable from electromagnetic radiation, in particular wherein the data stream comprises a continuous or discrete time-based characteristic signal, wherein the characteristic signal comprises at least two main components associated with a signal space, the signal space comprising complementary channels for representing the characteristic signal, the main components of the characteristic signal being related to respective complementary channels of the signal space. The invention further addresses distortion reduced signal detection.

BACKGROUND OF THE INVENTION

WO 2011/021128 A2 discloses a method and a system for image analysis, including:
obtaining a sequence of images;
performing a vision-based analysis on at least one of the sequence of images to obtain data for classifying a state of a subject represented in the images;
determining at least one value of a physiological parameter of a living being represented in at least some of the sequence of images, wherein the at least one value of the physiological parameter is determined through analysis of image data from the same sequence of images from which the at least one image on which the vision-based analysis is performed is taken; and
classifying a state of the subject using the data obtained with the vision-based analysis and the at least one value of the physiological parameter.

The document further discloses several refinements of the method and system. For instance, the use of remote photoplethysmographic (PPG) analysis is envisaged. In general, in the field of image processing enormous progress was made in that profound analyses of the recorded data were enabled. In this context, it could be envisaged to extract information from recorded data in a way so as to enable detailed conclusions regarding the physical condition or even the well-being of an observed living individual.

WO 2011/042858 A1 discloses a further method and system addressing processing a signal including at least a component representative of a periodic phenomenon in a living being. Additional basic approaches to remote photoplethysmography are described in Verkruysse, W. et al (2008), "Remote plethysmographic imaging using ambient light" in Optics Express, Optical Society of America, Washington, D.C., USA, vol. 16, no. 26, pp. 21434-21445.

However, the recorded data, such as captured reflected or emitted electromagnetic radiation, especially recorded image frames, always comprises, beside of the desired signal to be extracted therefrom, further signal components deriving from overall disturbances, by way of example, such as noise due to changing luminance conditions or a movement of observed objects. Hence, a detailed precise extraction of the desired signals still poses major challenges for the processing of such data.

Although considerable progress in the field of computing performance has been made, it is still a challenge to provide for instant image recognition and image processing enabling immediate, so to say, on-line detection of desired vital signals. This applies in particular to mobile device applications commonly lacking of sufficient computing power. Furthermore, data transmission capacity can be restricted in several applications.

A possible approach to this challenge may be directed to providing well-prepared and steady ambient conditions when capturing a signal of interest in which the desired signal component is embedded so as to minimize disturbing signal components overlaying the signal. However, such laboratory conditions cannot be transferred to everyday field applications as high efforts and preparation work would be required therefor.

After all, vital signal detection is made even more difficult when amplitudes and/or nominal values of disturbing signal components are much larger than amplitudes and/or nominal values of desired signal components to be extracted. Potentially, the magnitude of difference between the respective components can be expected to even comprise several orders. This applies in particular to remote PPG.

SUMMARY OF THE INVENTION

It is therefore an object of the present invention to provide a system and a method for extracting information from detected characteristic signals providing further refinements facilitating obtaining the desired signals with higher accuracy.

Furthermore, it would be advantageous to provide a device and method even adapted for enabling an extraction of the desired signals under considerably poor ambient conditions, e.g. small signal-to-noise ratio, varying luminance conditions and/or steady or even unsteady movements of the object to be observed. It would be further advantageous to provide a device adapted for being less susceptible to disturbances influencing the captured signals to be processed and analyzed.

In a first aspect of the present invention a system for extracting information from detected characteristic signals is presented, the system comprising:

an interface for receiving a data stream derivable from electromagnetic radiation reflected by an object, the data stream comprising a continuous or discrete time-based characteristic signal, the characteristic signal comprising at least two main components associated with a signal space, the signal space comprising complementary channels for representing the characteristic signal, the main components of the characteristic signal being related to respective complementary channels of the signal space, a converter means for mapping the characteristic signal to a defined component representation under consideration of a substantially linear algebraic signal composition model so as to specify a linear algebraic equation, the characteristic signal being at least substantially composed of a physiologic reflection component and a disturbing reflection component, wherein the physiologic reflection component comprises a basic reflection portion attributable to basic physiologic properties of the object to be observed and an indicative reflection portion attributable to at least one at least partially periodic vital signal, wherein the basic reflection portion comprises a basic reflection index element and a basic reflection coefficient, wherein the indicative reflection portion comprises an indicative reflection index element and a time-dependent indicative reflection coefficient, the indicative reflection coefficient being highly indicative of the at least one at least partially periodic vital signal of interest, wherein the disturbing reflection component comprises a disturbing reflection index element and a disturbing reflection coefficient, a processing means for at least partially solving the linear algebraic equation under consideration of an at least approximate estimation of the orientation of the basic reflection index element, the indicative reflection index element and the disturbing reflection index element so as to derive an expression highly indicative of the at least one at least partially periodic vital signal, the highly indicative expression at least comprising the indicative reflection coefficient.

Object motion and changing illumination conditions pose major challenges for signal detection, in particular when instant signal detection is demanded. For instance, detected illumination changes can be caused by object motion. This applies in particular when object tracking is subjected to restrictions, such as time delay, or even when illumination is only consistent in a very small area. Furthermore, illumination conditions can deteriorate due to unsteady illumination sources, e.g., varying ambient light. This applies in particular for signal detection based on remotely captured data.

The present invention is based on the insight that the characteristic signals can be decomposed into signal portions attributable to several phenomena. Having this relationship in mind, the signal extraction can be improved in that estimations concerning the orientation of several signal portions can be applied so as to simplify the underlying problem.

In other words, when "mapping" the characteristic signal to the defined component representation and "splitting" the signal into index elements (e.g., unit vectors) and coefficients representing respective magnitudes, a complex issue can be transferred to an expression comprising simplified sub issues. Hence, data processing can be focussed on these sub issues. Assumptions and estimations can be directed to sub issues and may at least partially contribute in treating the complex issue. In particular, the orientation of the disturbing reflection component can be estimated to some extent. Consequently, the characteristic signal can be at least partially compensated for the disturbing reflection component. The signal-to-noise ratio can be improved in this way. Thus, downstream signal analysis can be simplified, even under considerably challenging conditions.

The data stream can comprise a data sequence, e.g., a series of image frames comprising color information, such as RGB images. The image frames can represent the object of interest and further elements. Basically, the further elements are not indicative of the desired signals to be extracted from the data stream. In this connection, it can be envisaged that the characteristic signal comprises three (e.g. R, G, and B) or even more main components.

There exist several embodiments of the converter means and the processing means. In a first, fairly simple embodiment both, the converter means and the processing means, are embodied by a processing unit, in particular a processing unit of a personal computer or a mobile device, which is driven by respective logic commands. Such a processing unit may also comprise suitable input and output interfaces.

However, in the alternative, each of the converter means and the processing means can be embodied by a separate processing unit driven or driveable by respective commands. Hence, each respective processing unit can be adapted to its special purpose. Consequently, a distribution of tasks may be applied, wherein distinct tasks are processed, for instance, executed on a single processor of a multi-processor processing unit, or, again referring to a personal computer, image processing-related tasks are executed on an image processor while other operational tasks are executed on a central processing unit.

It goes without saying that further signal optimization measures can be applied to the data stream comprising the characteristic signals. These measures can comprise motion compensation, pattern detection, e.g., face detection, or normalization measures. Normalization can render signal components at least partially independent from overall disturbances. In the context, it is reminded that under everyday condition the signals of interest are considerably small compared to the non-indicative disturbances. Furthermore, upstream and/or downstream filters can be utilized so as to attenuate potentially non-indicative portions of the data stream.

According to a further aspect of the device, the at least one at least partially periodic vital signal is selected from the group consisting of heart rate, heart beat, respiration rate, heart rate variability, Traube-Hering-Mayer waves, and oxygen saturation, and wherein the signal space is an additive or subtractive color signal space, wherein the at least two main components represent respective distinct color components indicated by the complementary channels, wherein the complementary channels are related to defined spectral portions.

Advantageously, at least some of these vital signals can be converted into one another. Slight pulsations or oscillations of the characteristic signals can be analyzed and interpreted so as to arrive at the detection of the desired vital signals. Furthermore, it is understood that, in general, the desired vital signal(s) can be derived directly or indirectly from at least one at least partially periodic signal the object of interest exhibits. It goes without saying that the device and method of the invention can be combined with further detecting and analyzing measures so as to further enhance the signal extraction.

For instance, an RGB signal space may be applied. Alternative signal spaces may comprise or be derived from YUV, CIE XYZ, HSV, HSL, sRGB and xvYCC signals. Also derivates thereof can be utilized. It should be noted that basically linear RGB signals can be utilized for the desired signal detection. Therefore, non-linear signal spaces (e.g. gamma corrected signals) can be transformed accordingly. It can be further envisaged to combine several distinct signal spaces, at least partially, so as to provide a broader spectral basis for the required analyzing processes. For instance, so-called RGBY signals can be applied as well. In an RGBY signal space in addition to red, green and blue also yellow signals can carry color information.

In case the input data stream is related to a subtractive color model, e.g., CMYK, the data can be transferred accordingly so as to arrive at an additive signal space.

Further spectral components can be utilized for extracting the desired vital signal(s) from the data stream. In this connection, also infrared radiation components can be applied. For instance a ratio between red and infrared signals can be highly indicative of the desired signals. Also infrared radiation can undergo specular reflectance. It can be also envisaged to add infrared signals to an RGB signal space.

According to an even further aspect, the device comprises an extractor means for extracting the vital signal from the computed highly indicative expression, preferably the vital signal is extracted under consideration of the indicative reflection coefficient or of a ratio of the indicative reflection coefficient and the basic reflection coefficient.

For instance, the indicative reflection coefficient can be divided by the basic reflection coefficient or a mean of the basic reflection coefficient. A suitable intensity normalization can be achieved in this way. Consequently, the desired signal can become smoothened which could be considered desirable for further signal processing measures.

According to another advantageous embodiment of the device, the basic reflection portion is at least substantially indicative of a mean tissue color the object of interest exhibits, wherein the indicative reflection portion is at least substantially indicative of an at least partially periodic pulsation of the tissue color of the object of interest, and wherein the disturbing reflection component is at least substantially indicative of disturbing specular reflection.

For instance, a considerable portion of illumination-related disturbances can be explained by specular reflection. Specular reflectance is the "perfect" reflection of incident radiation at an interface. Basically, an incident ray corresponds to a reflected ray. An angle of reflection equals an angle of incidence. In other words, specular reflection implies mirror-like reflection at surfaces and interfaces. Furthermore, the reflected ray is highly indicative of the source of electromagnetic radiation, namely the illumination source. This relationship can be exploited so as to create and solve the linear algebraic equation representing a composition model of the characteristic signal.

It is understood that mainly diffuse reflection provides the desired vital signals. Diffuse reflection substantially comprises body reflection rather than interface reflection. For instance, body reflection is influenced by slight changes of the color of an area of interest of the body. Color changes can be caused, inter alia, by vascular pulsation due to blood circulation. The desired vital signals can be derived therefrom. Furthermore, incident radiation can be absorbed to some extent. However, the detectable reflected signals most probably comprise a disturbing specular reflection portion. Specular reflection basically "mirrors" incident radiation without being influenced by object properties present under the interface, e.g., the top surface of the skin. Especially perspiring skin areas and oily or greasy skin areas are highly susceptible to specular reflections. Under certain circumstances, e.g., sports practice, workouts, physically demanding work, or even due to illness, a huge portion of electromagnetic radiation reflected by the object can be related to specular reflectance. Thus, the characteristic signal can be supposed to have a poor, i.e. reasonably small, signal-to-noise ratio.

According to yet another aspect of the device, the estimated indicative reflection index element is obtained under consideration of an expression comprising the estimation of the basic reflection index element and a normalized expression of a predetermined exemplary indicative reflection index element.

An initial or moving estimation of a sample indicative reflection index element combined with a respective normalization so as to avoid skin type dependent influences can be considered a suitable approach to solving the linear algebraic equation built up by the converter means.

It is should be understood that a predetermined exemplary indicative reflection index element obtained during exemplary measurements can enable a determination of further indicative reflection index elements of objects to be observed when the respective basic reflection index element is determined. Basically, the basic reflection index element can be exploited for the desired estimation of the indicative reflection index element. A normalization applied to the exemplary indicative reflection index element can be directed to attenuate skin type dependent influences, at least to a certain extent. Consequently, the normalized (skin type independent) indicative reflection index element can be combined with the basic reflection index element so as to "replace" the present indicative reflection index element According to an advantageous alternative approach, the estimated indicative reflection index element is considered orthogonal to a signal plane spanned by the basic reflection index element and the disturbing reflection index element, wherein the estimated disturbing reflection index element is at least substantially aligned with a luminance index element being indicative of characteristics of an electromagnetic radiation source affecting the object of interest.

As mentioned above, specular reflection basically "mirrors" incident radiation. Consequently, the disturbing reflection index element can be considered exhibiting the color of the radiation source emitting the reflected radiation. Commonly, at least substantially white light is emitted by the radiation source. As a result, for specular reflection, the specularly reflected radiation detected by the sensor means also exhibits white radiation (light). When agglomerating main components of an indicative pattern so as to arrive at the characteristic signals, the specular reflection related disturbing reflection component basically causes a "signal offset" aligned with the disturbing reflection index element. The length (or magnitude) of the signal offset can be attributed to the fraction of the indicative pattern subjected to specular reflection. For white light, the disturbing reflection index element can be considered parallel to a diagonal vector traversing the signal space, the diagonal vector representing a radiation source characteristic. In case an (unitary) RGB signal space is applied, the diagonal vector basically starts at the black point, e.g., (0,0,0), and ends at the white point, e.g., (1,1,1), of the signal space. Hence, the disturbing reflection index element can be represented by the vector (1,1,1). It goes without saying that a (length) normalization can be applied to the respective vector since the disturbing reflection index element is indicative of a direction (i.e. a spatial orientation) rather than a distinct value expression comprising length information.

In case the whole agglomerated pattern is subjected to specular reflection, the characteristic signal substantially corresponds to the disturbing reflection component which can be considered equal to the diagonal vector. In case the observed pattern is only partially affected by specular reflection, the characteristic signal is partially composed of the disturbing reflection component which can be considered parallel to but respectively shorter than the diagonal vector.

It should be understood that the "diagonal vector" can be adapted accordingly in case non-white light is applied.

Further supposing that the estimated indicative reflection index element can be considered orthogonal to a plane spanned by the basic reflection index element and the disturbing reflection index element is an adequate assumption since the fluctuations of the desired vital signal in the signal can be assumed to be parallel with neither the basic reflection index element nor the disturbing reflection index element. In other words, assuming that the indicative reflection index element can be considered a (normalized) cross product of the basic reflection index element and the disturbing reflection index element is an advantageous approach in case the normalized expression of the (predetermined) exemplary indicative reflection index element cannot be determined in advance.

According to yet an even further aspect, the estimated basic reflection index element is derived from agglomerated main components of the characteristic signal of an indicative area of the object of interest, wherein the estimated disturbing reflection index element is at least substantially aligned with a luminance index element being indicative of characteristics of an electromagnetic radiation source affecting the object of interest, preferably the device is further adapted to apply an initial determination of the basic reflection index element when observing the object of interest.

For instance, a face portion of an object of interest can be observed. When tracking the face portion, a normalization can be applied so as to summarize single (pixel) values of a respective (pixel) pattern overlaying the face portion. Consequently, the characteristic signal can comprise a single agglomerated value. The characteristic signal can be normalized for object motion and/or changing illumination in this way.

According to an advantageous variant of this embodiment, the estimated indicative reflection index element is considered at least substantially orthogonal to the basic reflection index element and at least substantially orthogonal to the disturbing reflection index element.

According to an even further embodiment, a logarithmic signal representation is applied to the defined component representation, preferably an assumed ratio between the basic reflection coefficient and the disturbing reflection coefficient is taken into consideration for the determination of the indicative reflection coefficient.

This embodiment can be particularly suitable when also utilizing signal spaces comprising logarithmic scales. For instance, a log RGB signal space can be applied for representing the characteristic signals. In general, logarithmic data representation can address expected poor signal-to-noise ratios by reducing the representation of wide-ranging values to smaller scopes. Furthermore, logarithms can facilitate data computing since complex computations can be replaced or at least approximated by simplified computing operations of logarithmic values. Moreover, logarithmic data representation allows for further simplified representations such as Taylor series. Hence, for instance, for data processing basically relying on a ratio of two distinct values this ratio can be transferred into a logarithmic representation which can be transferred into an (approximated) Taylor series. Consequently, a division term can be readily replaced by a difference term.

According to a variant of this embodiment, a basis change is applied to the defined component representation so as to ensure that a mean value of the indicative reflection coefficient is greater than zero, wherein the vital signal can be derived from a transformed representation of the indicative reflection coefficient.

According to another aspect of the invention, data processing further comprises a normalization of the characteristic signal under consideration of the basic reflection index element.

According to a further aspect of the invention, the disturbing reflection index element is obtained under consideration of an expression comprising a predetermined normalized value of the basic reflection index element obtained under consideration of an assumed standard orientation of a luminance index element being indicative of characteristics of an electromagnetic radiation source affecting the object of interest.

In this context, it should be understood that in some cases an estimated (common) basic reflection index element can be considered. For instance, when the radiation source basically emits white light, the basic reflection index element can be estimated to be independent of the skin type of the object of interest, at least to a certain extent. Having this estimation in mind, the actual basic reflection index element can be replaced by the estimated basic reflection index element for further processing.

According to a further advantageous variant, the device further comprises a buffer means for buffering the characteristic signal and a resulting representation of the basic reflection coefficient, the indicative reflection coefficient and the disturbing reflection coefficient for a defined period, wherein the processing means is further adapted to apply a Fourier transformation to the buffered indicative reflection coefficient so as to determine dominant frequency components thereof, wherein the basic reflection coefficient, the indicative reflection coefficient and the disturbing reflection coefficient are transferred to a transformed signal representation comprising inner products of respective coefficients, wherein the indicative reflection index element is determined under consideration of the transformed signal representation.

The indicative reflection coefficient can be assessed for eligibility for further signal processing in this way. Basically, when the Fourier transformation of the buffered indicative reflection coefficient shows a clean signal peak related to a respective frequency, further processing can be applied to the indicative reflection coefficient. In this connection, it could be envisaged to apply a certain threshold to a ratio of the largest signal peak and further signal peaks. The dominant frequency can be determined in this way.

In a further aspect of the present invention a method for extracting information from detected characteristic signals is presented, comprising the steps:

receiving a data stream derivable from electromagnetic radiation reflected by an object, the data stream comprising a continuous or discrete time-based characteristic signal, the characteristic signal comprising at least two main components associated with a signal space, the signal space comprising complementary channels for representing the characteristic signal, the main components of the characteristic signal being related to respective complementary channels of the signal space, mapping the characteristic signal to a defined component representation under consideration of a substantially linear algebraic signal composition model so as to specify a linear algebraic equation, the characteristic signal being at least substantially composed of a physiologic reflection component and a disturbing reflection component, wherein the physiologic reflection component comprises a basic reflection portion attributable to basic physiologic properties of the object to be observed and an indicative reflection portion attributable to at least one at least partially periodic vital signal, wherein the basic reflection portion comprises a basic reflection index element and a basic reflection coefficient, wherein the indicative reflection portion comprises an indicative reflection index element and a time-dependent indicative reflection coefficient, the indicative reflection coefficient being highly indicative of the at least one at least partially periodic vital signal of interest, wherein the disturbing reflection component comprises a disturbing reflection index element and a disturbing reflection coefficient, at least partially solving the linear algebraic equation under consideration of an at least approximate estimation of the orientation of the basic reflection index element, the indicative reflection index element and the disturbing reflection index element so as to derive an expression highly indicative of the at least one at least partially periodic vital signal, the highly indicative expression at least comprising the indicative reflection coefficient.

Advantageously, the method can be carried out utilizing the device for extracting information of the invention.

According to an even further aspect of the invention a computer program is presented, the computer program comprising program code means for causing a computer to carry out the steps of the method for extracting information of the invention when said computer program is carried out on a computer.

Preferred embodiments of the invention are defined in the dependent claims. It shall be understood that the claimed method has similar and/or identical preferred embodiments as the claimed device and as defined in the dependent claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
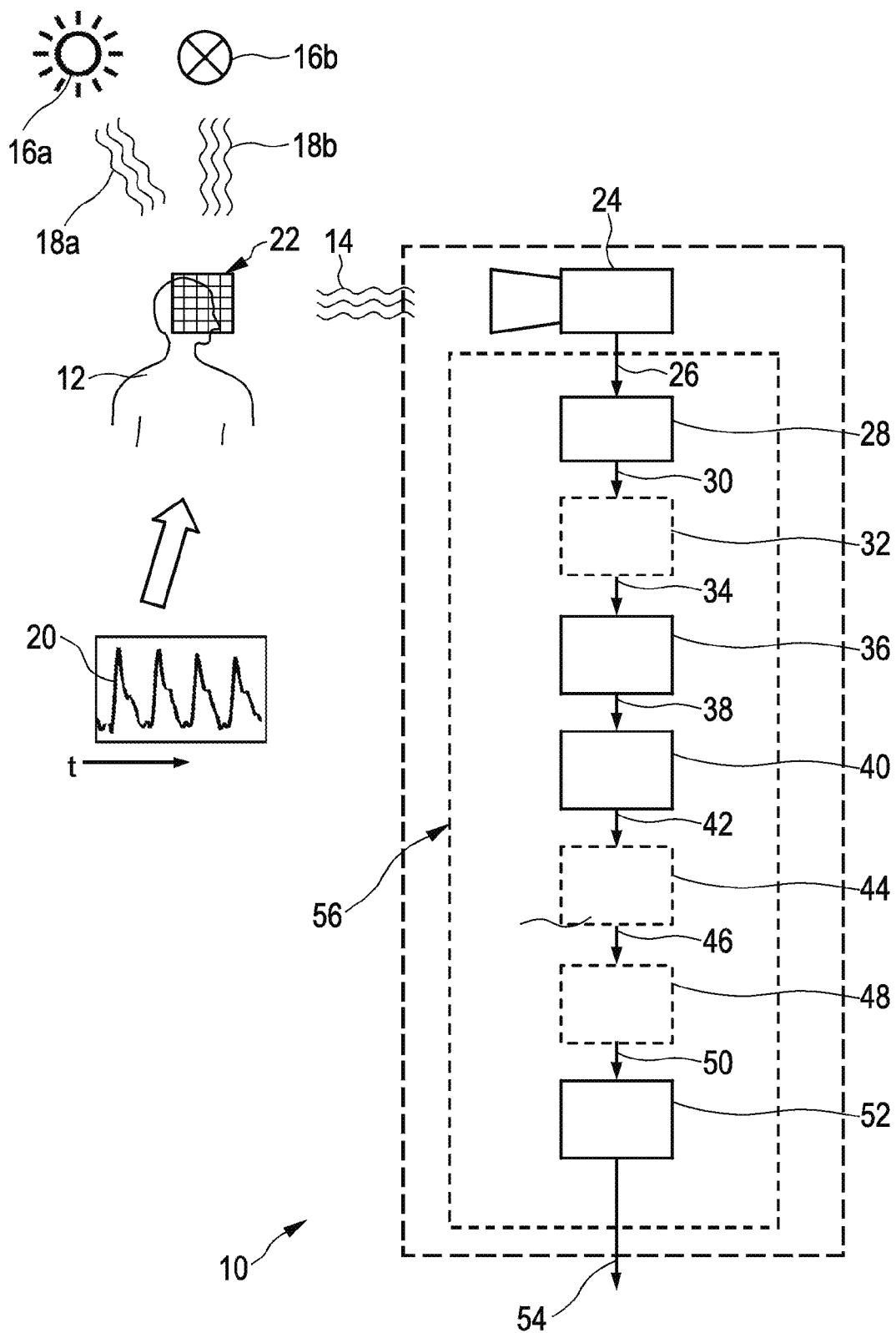
FIG. 1 shows a schematic illustration of a general layout of a device in which the present invention can be used.

FIG. 1 shows a schematic illustration of device for extracting information which is denoted by a reference numeral 10. For instance, the device 10 can be utilized for recording or processing image frames representing a remote object 12 for remote PPG monitoring. The image frames can be derived from electromagnetic radiation 14 reflected by the object 12. The object 12 can be a human being or animal, or, in general, a living being. Furthermore, the object 12 can be part of a human being highly indicative of a desired signal, e.g., a face portion, or, in general, a skin portion.

A source of radiation, such as sunlight 16a or an artificial radiation source 16b, also a combination of several radiation sources can affect the object 12. The radiation source 16a, 16b basically emits incident radiation 18a, 18b striking the object 12. For extracting information from the recorded data, e.g. a sequence of image frames, a defined part or portion of the object 12 can be detected by a sensor means 24. The sensor means 24 can be embodied, by way of example, by a camera adapted to capture information belonging to at least a spectral component of the electromagnetic radiation 14. It goes without saying that the device 10 also can be adapted to process input signals, namely an input data stream, already recorded in advance and, in the meantime, stored or buffered. As indicated above, the electromagnetic radiation 14 can contain a continuous or discrete characteristic signal which can be highly indicative of at least one at least partially periodic vital signal 20. The characteristic signal can be embodied by an (input) data stream 26. For data capturing, a potentially indicative portion of the object 12 can be masked with a pixel pattern 22. When agglomerating respective single pixel values of the additive components, a mean pixel value can be derived from the pixel pattern 22. In this way, the detected signals can be normalized and compensated for undesired object motion to some extent. The mean pixel value can be represented by a characteristic signal. In the following, the captured data stream 26 can be considered a representation of a certain area of interest of the object 12 which may cover a single pixel or, preferably, an agglomerated pixel area covering a plurality of pixels.

In FIG. 1 the vital signal 20 may allow several conclusions concerning heart rate, heart beat, heart rate variability, respiratory rate, or even oxygen saturation.

Common methods for obtaining such vital signals may comprise tactile heart rate monitoring, electrocardiography or pulse oximetry, for instance. To this end, however, obtrusive monitoring is required. As indicated above, an alternate approach is directed to unobtrusive remote measuring utilizing image processing methods.

The data stream 26 comprising the continuous or discrete characteristic signal can be delivered from the sensor means 24 to an interface 28. Needless to say, also a buffer means could be interposed between the sensor means 24 and the interface 28. Downstream of the interface 28 an input filter 32 can be provided to which a data stream 30 can be delivered. The input filter 32 can be considered optional, which is indicated by a dashed line. Input filter 32 can be adapted for filtering the data stream 30 delivered thereto. For instance, the input filter can comprise band bass filtering, high pass filtering and/or low pass filtering means. For some approaches, input filtering can be considered a suitable measure so as to remove undesired (frequency) portions from the data stream, at least to some extent. The input filter 32 can be embodied by means of hardware or software. A filtered data stream 34 can be obtained in this way.

The filtered data stream 34 can be delivered to a converter means 36 so as to build up a defined data representation under consideration of (assumed) components of the data stream 26, 30, 34. To this end, a characteristic signal comprised in the data stream 26, 30, 34 is basically equated to a signal composition model which incorporates a physiologic reflection component and a disturbing reflection component. Moreover, the physiologic reflection component can be attributed to a basic reflection portion and an indicative reflection portion. The indicative reflection portion is considered highly indicative of the signal of interest. By "establishing" an equation implying these relationships, the problem underlying the signal extraction can be simplified and prepared for further suitable signal processing measures.

Downstream of the converter means 36 a processing means 40 is provided to which a converted data stream 38 can be delivered. The converter means 36 is adapted for at least partially solving the equation set up by the converter means 36. Consequently, a processed data stream 42 can be obtained. For instance, the processed data stream 42 can comprise a value related to the indicative reflection portion, for instance, an expression indicating a temporal "strength" or "energy" of the indicative reflection portion. Basically, the indicative reflection portion is supposed to pulsate slightly in accordance with the desired signal of interest.

The processed data stream 42 can be further optimized by utilizing an optional intensity normalization means 44. Intensity normalization may comprise a consideration of a signal component supposed not to be indicative of the vital signal of interest but rather to be indicative of overall intensity changes. For instance, intensity changes can comprise varying illumination conditions. Consequently, a normalized data stream 46 can be obtained.

A further optional data processing measure can be carried out by an output filter 48. The output filter 48 can further enhance the signal quality. The output filter 48 can comprise band bass filtering, high pass filtering and/or low pass filtering means so as to enhance a potentially indicative (frequency) signal portion.

A filtered data stream 50 can be delivered to an extractor means 52 which can be adapted for extracting the vital signal of interest 20 from the filtered data stream 50. For instance, components of the characteristic signal involving an indicative reflection portion related term can be compared so as to derive a highly indicative term. Consequently, an extracted output signal 54 can be created. Furthermore, the extractor means 52 can be adapted for further signal processing, e.g., detection of a dominant signal peak, such as a heart rate indicative frequency peak.

The input filter 32, the converter means 36, the processing means 40, the intensity normalization means 44, the output filter 48, and the extractor means 52 can be jointly embodied by a common processing unit 56, e.g. a central processing unit having a single processor or multiple processors. Also the interface 28 can be connected thereto in the common processing unit 56 housing the respective subcomponents. By way of example, the processing unit 56 can be embodied by a personal computer driven by respective logic commands. In case the sensor means 24 is also jointly connected to the interface 28 by means of hardware, a capturing unit arranged at a higher level may house the respective subcomponents.

However, in the alternative, it can be envisaged to combine a separate sensor means 24 with the processing unit 56. This connection can be established by means of cable links or by means of wireless links. In place of the sensor means 24 also a storage means comprising prerecorded data could be connected to the processing unit 56.

The following section describes exemplary approaches to remote photoplethysmography utilizing several aspects of the device and method of the invention. It should be understood that single steps and features of the shown approaches and embodiments can be extracted from the context of the explanation. These steps and features can be therefore part of separate embodiments still covered by the scope of the invention.

Unobtrusive vital signal monitoring using remote detectors has been introduced. For instance, video cameras can be utilized. By way of example, the vital signals of interest can comprise heart rate, heart beat, or respiratory rate. In particular, some of these attempts can be referred to as remote photoplethysmography (PPG).

A possible approach for remote PPG can comprise algorithms tracking the average skin-tone of an object of interest, which varies, or, fluctuates, with the blood volume and blood oxygenation. In general, however, this general approach is very sensitive to motion, local variations in skin-tone, and illumination level/spectrum, since the desired signal becomes distorted accordingly when affected by these phenomena.

So-called additive distortion can be considered a huge challenge for these basis approaches. Basically, additive distortion, for instance, a change in specular reflectance, does not comprise the signal of interest, e.g. a heart beat signal. Hence, the performance of known approaches and algorithms may deteriorate significantly when facing additive distortion.

Standard photoplethysmography (PPG) can be used to obtain desired vital signals in a non-invasive way. For instance, the cardiovascular pulse can be monitored. However, standard PPG utilizes attachments firmly fixed to an object of interest, e.g. to a fingertip or an earlobe. Thus, standard PPG can still be considered an obtrusive method. In general, PPG utilizes reflectance or transmission of light which can be considered to change due to a local change of the blood volume or a change in the oxygen saturation. For instance, light emitting diodes (LED) at different wavelengths, e.g., red and infrared light, can be used for generating radiation directed to the object of interest. Furthermore, a photodiode detector can be used so as to detect the light changes. Consequently, e.g., to estimate the heart rate, the ratio v of two time signals $v_r$ and $v_{ir}$, corresponding to the photodiode response to the red light and the infrared light, can be analyzed:

$$v(n) = \frac{\frac{v_r(n)}{\overline{v}_r}}{\frac{v_{ir}(n)}{\overline{v}_{ir}}}, \quad (1)$$

wherein $\overline{v}_r$ and $\overline{v}_{ir}$ correspond to mean values of the signals $v_r$ and $v_{ir}$, respectively. The ratios are considered so as to normalize the signals for the intensity of the LEDs and for the skin color. Basically, the signal v can exhibit the cardiovascular pulse, and the heart rate can basically be determined through a frequency analysis of the resulting signal v.

Equation (1) can be rewritten when estimating that a mean $\overline{v}$ of the signal v basically equals one, e.g. due to a unitary normalization. Since alternating behavior (e.g., related to the heart rate) of the signal v can be of particular interest, the mean $\overline{v}$ (i.e., 1) can be subtracted accordingly:

$$v(n) - 1 = \frac{\frac{v_r(n)}{\overline{v}_r}}{\frac{v_{ir}(n)}{\overline{v}_{ir}}} - 1 = \frac{\frac{v_r(n)}{\overline{v}_r} - \frac{v_{ir}(n)}{\overline{v}_{ir}}}{\frac{v_{ir}(n)}{\overline{v}_{ir}}}.$$

In this context, it should be understood that the red over infrared ratio is an exemplary approach to the extraction of the desired signal. For instance, also a red over green ratio could be utilized. Further ratios related to signal components related to defined spectral portions can be considered as well.

When further assuming that the denominator of the above expression is close to one, it can be concluded that this expression can be approximated by a difference signal term:

$$\tilde{v}(n) = v(n) - 1 \approx \frac{v_r(n)}{\overline{v}_r} - \frac{v_{ir}(n)}{\overline{v}_{ir}}. \quad (2)$$

However, for cases involving disturbances that are "visible" in the infrared radiation indicative denominator term, especially for remote PPG applications, this approximation is considered inappropriate.

Alternatively, the logarithm operator can be utilized for simplifying the expression of the signal v provided in equation (1) which leads to $$\hat{v}(n) = \log v(n) \quad (3)$$

$$= \log \frac{v_r(n)}{\overline{v}_r} - \log \frac{v_{ir}(n)}{\overline{v}_{ir}}$$

$$= \log\left(1 + \frac{v_r(n)}{\overline{v}_r} - 1\right) - \log\left(1 + \frac{v_{ir}(n)}{\overline{v}_{ir}} - 1\right)$$

$$\approx \frac{v_r(n)}{\overline{v}_r} - \frac{v_{ir}(n)}{\overline{v}_{ir}},$$

considering an assumption according to which the ratios $v_r(n)/\bar{v}_r$, and $v_{ir}(n)/\bar{v}_{ir}$ are both close to one, and further utilizing a Taylor series of the logarithm operator for an approximation of the logarithmic expression, e.g.

$$\log(1+x) = x - \frac{1}{2}x^2 + \frac{1}{3}x^3 - O(x^4) \approx x.$$

An advantage of the logarithm operator can be seen in the fact that basically a luminance normalization (for instance, directed to the intensity of the light sources, e.g. LEDs, and to the skin color the object of interest exhibits) can be avoided as the logarithmic operator leads to $$\log\frac{v_r(n)}{v_{ir}(n)} = \log v_r(n) - \log v_{ir}(n) \quad (4)$$
$$= \log\frac{\bar{v}_r}{\bar{v}_r}v_r(n) - \log\frac{\bar{v}_{ir}}{\bar{v}_{ir}}v_{ir}(n)$$
$$= \log\frac{\bar{v}_r}{\bar{v}_{ir}} + \log\frac{v_r(n)}{\bar{v}_r} - \log\frac{v_{ir}(n)}{\bar{v}_{ir}}$$
$$\approx \frac{\bar{v}_r}{\bar{v}_{ir}} + \frac{v_r(n)}{\bar{v}_r} - \frac{v_{ir}(n)}{\bar{v}_{ir}},$$

wherein the term $$\log\frac{\bar{v}_r}{\bar{v}_{ir}}$$

can be removed when considering band pass filtering of the signals so as to reduce distortions outside a frequency range of interest.

Basically, two (approximately discrete) wavelengths, e.g., red and infrared, can be used to measure the signal of interest, e.g., the cardiovascular pulse. However, the present approach is not limited to these wavelengths. However, since basic remote PPG approaches relying on camera based measurement have been introduced, also red, green and blue signals (RGB) become available for signal processing and detecting the vital signal of interest.

Still, remote measurement is subjected to several major disturbing influences. For instance, specular reflectance as well as undesired object motion is observed by the camera. Consequently, the signal-to-noise ratio can deteriorate significantly. In this connection, it would be desirable to account for these disturbances. Being aware of main disturbances and considering basic properties thereof, the signal detection can be highly improved.

In the following a dichromatic reflection model is introduced which can be considered an appropriate approach to enable the detection of the desired signals, even when facing a poor signal-to-noise ratio. The dichromatic reflection model models how light (or, in general, electromagnetic radiation) interacts with both a medium that comprises a surface layer reflecting a fraction of incident light, and a tissue layer comprising colorant producing scattered reflection and (skin) coloration.

Figure 2:
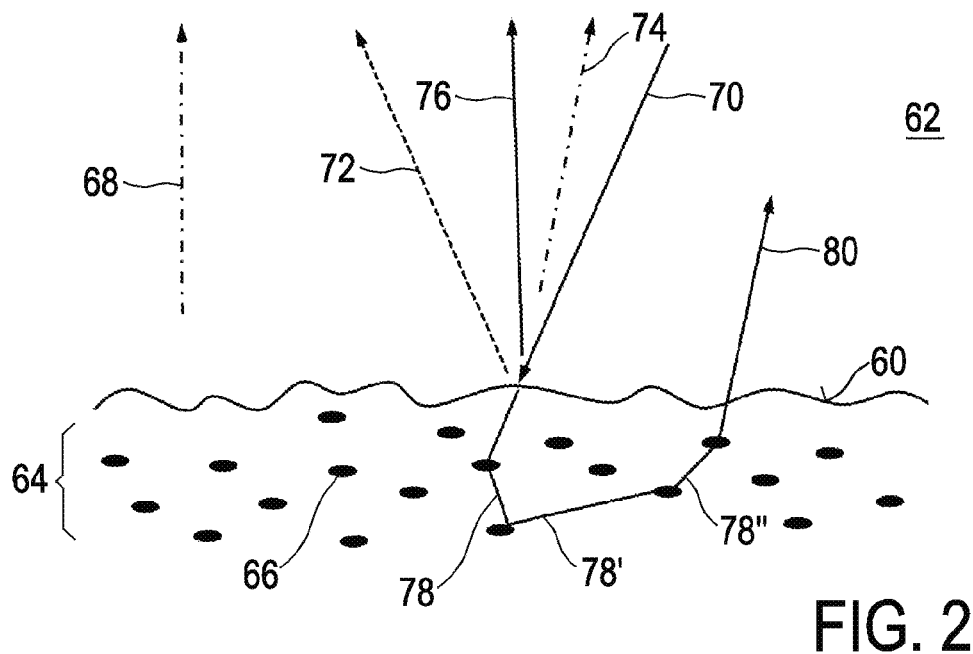
FIG. 2 shows a schematic illustration of a reflectance model utilizing a body reflection and interface reflection approach.

In this connection, reference is made to FIG. 2 illustrating reflection of incident radiation 70 at an interface 60 between two media 62, 64. Reference numeral 62 denotes air through which incident radiation 70 is transmitted. Reference numeral 64 denotes a skin tissue to which incident radiation 70 is directed. The interface 60 is interposed between the air 62 and the skin tissue 64. The interface 60 can be considered as the top surface of the skin. The skin tissue 64 may comprise colorant 66 which slightly fluctuates with the signal of interest, e.g., the heart rate. The interface or top surface 60 may comprise a macroscopic surface normal 68 and microscopic surface normals 74, the latter attributable to microscopic surface unevenness. Hence, even incident radiation 70 subjected to (perfect) specular reflection at the interface 60 can be reflected at an reflection angle corresponding to the microscopic surface normal 74 rather than the macroscopic surface normal 68. The reflected radiation is denoted by reference numeral 76. A reflected radiation to be expected with knowledge of the macroscopic surface normal 68 is denoted by reference numeral 72. However, for the following elucidation the microscopic surface normal 74 can be equated with the macroscopic surface normal 68.

Furthermore, a considerable component of the incident radiation 70 is reflected by skin tissue colorant 66 rather than the interface 60. The reflection may comprise multiple reflections as indicated by reference numerals 78, 78', 78". As the skin tissue colorant 66 is distributed inhomogeneously in the skin tissue 64 and respective colors may vary over time, the so-called body reflection can be considered substantially diffuse reflection. Reflected radiation due to body reflection is denoted by reference numeral 80. Thus, beside of the specular reflection component 76 also a diffuse scattered reflection component 80 can be reflected by the object of interest.

Hence, a part of incident light or radiance is reflected by a diffuse reflection component, namely the body reflection component 80, which has traveled through the skin and represents skin colors including variations thereof due to the desired vital signals, e.g., heart rate. This reflection component is highly indicative of the signals of interest.

On the contrary, the specular reflection component 76 directly reflected at the top surface 60 of the skin is mainly indicative of the color of the illuminant and does not comprise considerable signals of interest.

Therefore, two fractions of radiance reflected by the object of interest may occur. In combination these fractions form the observed characteristic signals, e.g., the observed color. Illumination conditions may vary over time, e.g., due to object motion. Consequently, also the characteristic signals may vary widely over time.

Figure 3:
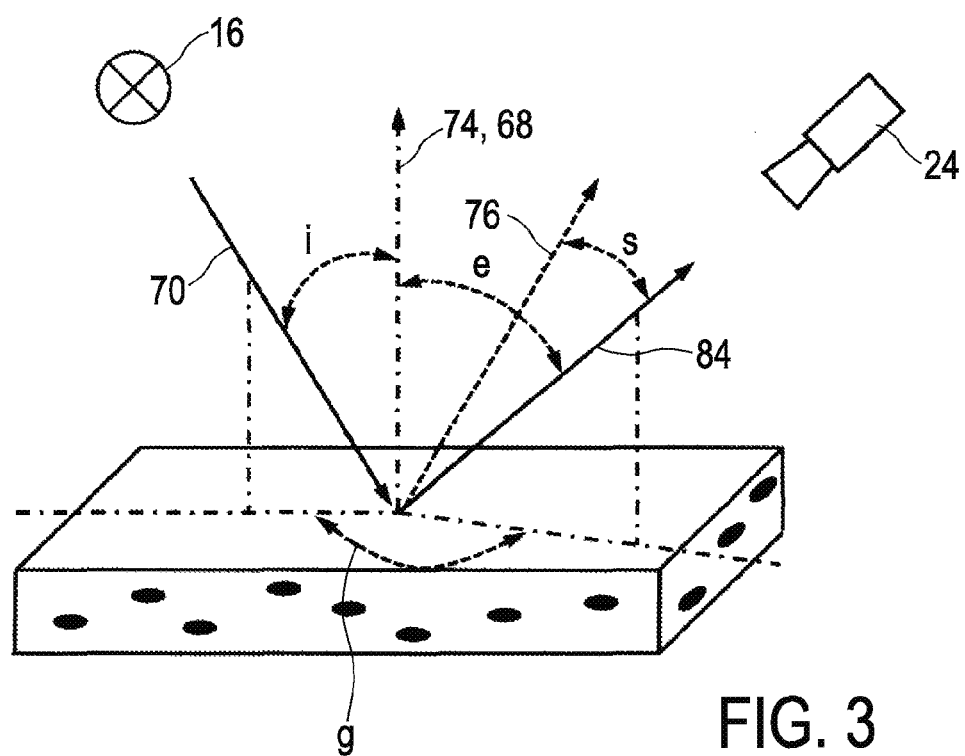
FIG. 3 shows a further exemplary schematic illustration of a reflectance model.

The dichromatic reflection model basically states that the total radiance P of the reflected light for the wavelength λ, is the sum of two independent parts:

$$P(\lambda,i,c,g) = m_s(i,e,g) \cdot s(\lambda) + m_b(i,e,g) \cdot b(\lambda) \quad (5)$$

where i is the angle of incidence, e the angle of emittance, and g the phase angle as illustrated in FIG. 3. In FIG. 3, reference sign 70 corresponds to the direction of the illumination (incident radiation). Reference signs 74, 68 denote respective surface normals which are unified in FIG. 3 for illustrative purposes. Reference sign 76 stands for a specular reflection component reflected at the interface of the object of interest. Reference sign 84 denotes a viewing direction. Furthermore, for completeness, FIG. 3 shows an angle s indicating the angle between the direction of specular reflection 76 and the viewing direction 84 indicating a position and/or orientation of the sensor means 24. In the following, the angle should not be confused with the spectral power distributions s of equation (5).

Equation (5) comprises two relative spectral power distributions s and b. Basically, s and b depend on the wavelength λ, of the radiation. Whiles can be considered an interface reflectance component, b can be considered a body reflectance component. The coefficients $m_s$ and $m_b$ substantially depend on geometry. The coefficients $m_s$ and $m_b$ can be referred to as geometric scale factors of the body reflectance component b and the interface reflectance component s.

For convenience, equation (5) can be transferred to a summarized vector space representation $$\underline{p} = m_s \underline{s} + m_b \underline{b} \quad (6)$$

when considering spectral response characteristics of the sensor means (e.g. camera) actually utilized. For instance, filter characteristic of the sensor means such as red, green and blue filters can be taken into account. In total, equation (5) can be integrated over a spectrum of the illumination applied so as to yield the total intensity of the reflected light. This results in equation (6) providing a dichromatic reflection model for a signal space, e.g. an RGB color space, for a specific point on a surface of interest, wherein magnitudes $m_s$ and $m_b$ can be considered as scalars. The vector $\underline{p}$ represents the measured color, or, the characteristic signal. The coefficients $m_s$ and $m_b$ can be considered magnitudes of reflection at the point in question. The vectors $\underline{s}$ and $\underline{b}$ represent the colors of the interface reflection (also referred to as specular reflection) and body reflection (also referred to as physiologic reflection) of the object of interest.

It can be assumed that the measured (overall) color $\underline{p}$ (also referred to as characteristic signal) represents a set of (pixel) points on the object surface, which can be colored more or less uniformly (skin color). Basically, geometry related factors differ from point to point. Therefore, the scale factors $m_s$ and $m_b$ can vary from point to point. However, the color $\underline{s}$ and $\underline{b}$ of the interface and body reflection substantially remain unchanged at all points on the surface of interest, since they can be considered spectral projections of $s(\lambda)$ and $b(\lambda)$ which do not vary with geometry. In other words, when applying vector representation, each pixel signal $\underline{p}$ lies in a plane spanned by both color vectors $\underline{s}$ and $\underline{b}$ (also referred to as dichromatic plane). Consequently, the colors $\underline{p}$ can be considered independent of the illumination conditions (comprising the same spectrum but different intensity).

According to an advantageous approach, the dichromatic reflection model can be extended by further assumptions regarding the body reflection vector $\underline{b}$, or, physiologic reflection component. As mentioned above, slight changes of the absorbance of the object's skin tissue can be detected so as to extract the vital signal of interest. In other words, the (actual) body reflection vector $\underline{b}$ (slightly) oscillates in time around a mean body reflection vector $\hat{\underline{b}}$. For convenience, it can be assumed that these oscillations can be described by a vector, or, at least linearly approximated by a vector. Consequently, the vector can be labeled as a heart beat vector h. Incorporating the vector h into the dichromatic reflection model can be considered an appropriate measure for extending the dichromatic reflection model so as to facilitate signal detection and processing. Consequently, the characteristic signal $\underline{p}$ (e.g., RGB values) of a pixel (or, pixel pattern) of interest can be described by a substantially linear combination of a (mean) body reflection vector $\hat{\underline{b}}$, the interface vector $\underline{s}$ and the heart beat vector h:

$$\underline{p} = c_0 \hat{\underline{b}} + c_1 h + c_2 \underline{s}.$$

For convenience, the hat of the mean body reflection vector $\hat{\underline{b}}$ can be dropped hereinafter:

$$\underline{p} = c_0 \underline{b} + c_1 h + c_2 \underline{s}. \quad (7)$$

It should be understood that the vector h, for instance the heart beat vector, is not a constant vector, but depends on the color of the illumination, the responsivity of the camera, the filter responses of the red, green and blue channel and the skin color of the subject. Basically, the same applies to the vectors $\underline{b}$ and $\underline{s}$. Consequently, the vector h should have to be determined for every sensor means (camera) and for every type of radiation source (illumination). However, based on the following elucidations it can be concluded that the skin type (i.e., the skin color) does not play a role. Therefore, in general, it can be considered sufficient to estimate the heart beat vector h for a sensor means under steady illumination conditions for an exemplary object of interest having a certain skin type. Subsequently, the (actual) heart beat vector h can be estimated on a case-by-case basis by using the estimate of the body reflection vector $\underline{b}$ for the actual skin type. Potentially, this insight can be exploited as follows: if the subject of interest remains still for a short period of time, for instance, a few seconds, the heart beat vector h can be easily determined in a mediate way through a principle component analysis applied to the mean red, mean green and mean blue values of the skin pixels of the object of interest in this short period of time. Basically, the respective mean red, mean green and mean blue values can be considered indicative of the actual body reflection vector $\underline{b}$.

In the alternative, the vector h can be derived via a consideration of indicative frequency peaks of the respective red, green and blue signals. To this end, for example, the Fourier transformation can be applied to the signals so as to obtain respective magnitude spectras. Considerable peaks that are at least substantially present in each of the red, green and blue signals at the same frequency can indicate the heart beat vector h. Consequently, respective red, green and blue peak magnitudes can be utilized for "constructing" the vector h. Hence, the orientation of the heart beat vector h can be determined. Needless to say, the heart beat vector h can be further transformed into a unit vector or something similar, since the vector h merely indicates the (assumed) orientation of the heart beat related signal portion $c_1 h$.

Figure 4A:
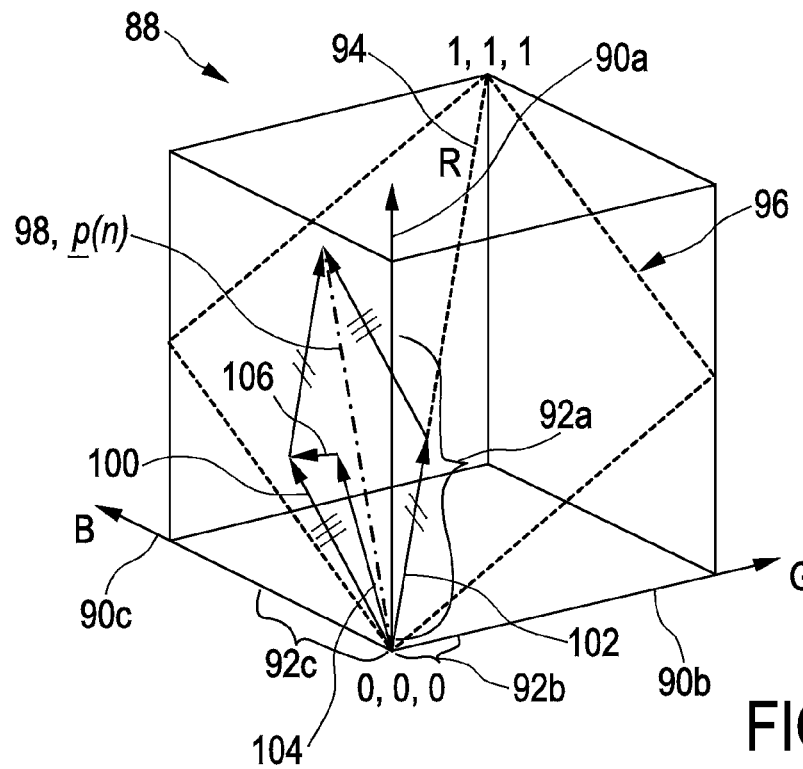
FIG. 4a shows an exemplary schematic illustration of a signal space comprising an index element representing a characteristic signal.
Figure 4B:
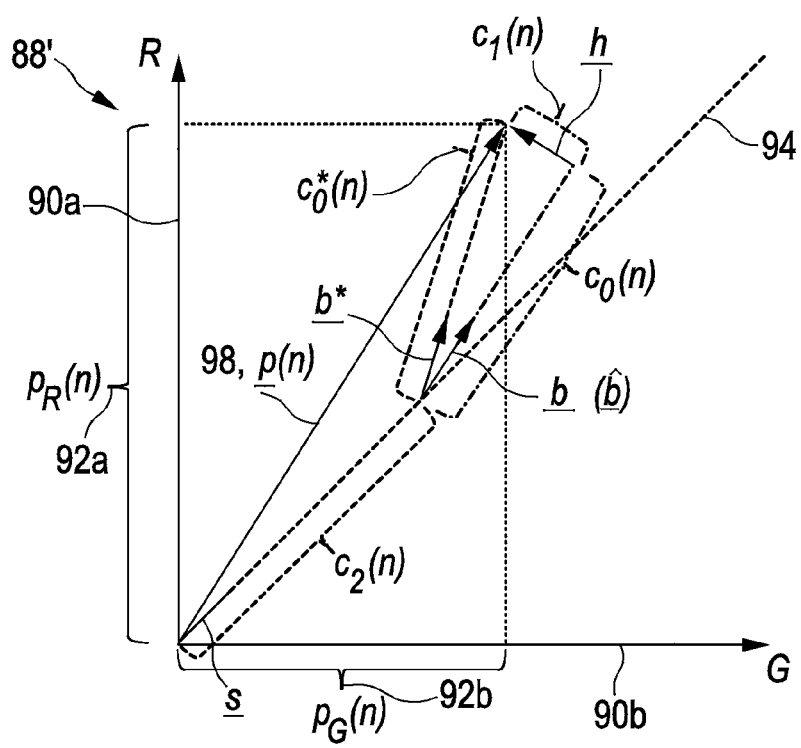
FIG. 4b shows a further exemplary simplified schematic illustration of a signal space by way of explanation.

In this connection, FIGS. 4a and 4b are referred to. FIG. 4a depicts an exemplary signal space 88, e.g. an RGB color space. The signal space 88 comprises complementary channels 90a, 90b, 90c indicative of spectral information, e.g., red, green and blue color channels. By way of example, the signal space 88 can be considered a "unitary" signal space, wherein components along the complementary channels 90a, 90b, 90c can take values between zero and one. Further value ranges departing from the zero and one range can be envisaged and treated accordingly. FIG. 4b shows a simplified signal space 88' merely comprising two complementary channels 90a, 90b for illustrative purposes. In others words, the signal space 88' can be considered a "slice" of the signal space 88. For instance, a characteristic signal 98, $\underline{p}$ can be expressed by main components 92a, 92b, 92c indicating intensity values (e.g., $p_R$, $p_G$ and $p_B$) the characteristic signal 98 (or, $\underline{p}$) is composed of that are related to the respective complementary channels 90a, 90b, 90c. Reference sign 94 indicates a luminance index element. The luminance index element 94 is indicative of a source of incident radiation, e.g. a light source. The luminance index element 94 can be considered a diagonal vector traversing the signal space 88. This applies in particular when the radiation source 16 basically emits plain white light. Preferably the "color" of the radiation source 16 equals the white point (e.g. 1,1,1) of the signal space 88.

According to the reflection model outlined above, the detected characteristic signal 98 (or, $\underline{p}$) can be considered an additive combination of a physiologic reflection component 100 and a disturbing reflection portion 102 (or, $c_2 \underline{s}$). The physiologic reflection component 100 can be further considered to be composed of a basic reflection portion 104 (or, $c_0 \underline{b}$, and $c_0 \hat{\underline{b}}$, respectively) and an indicative reflection portion 106

(or, $c_1 h$). In other words, the physiologic reflection component 100 can be considered a linear combination of the basic reflection portion 104 and the indicative reflection portion 106. The basic reflection portion 104 represents the mean body reflection vector $\underline{b}$ (or $\hat{\underline{b}}$) and a respective coefficient $c_0$. As outlined above, an (actual) body reflection vector $\underline{b}^*$ oscillates in time around the mean body reflection vector $\underline{b}$ (or $\hat{\underline{b}}$). Therefore, for the sake of completeness, FIG. 4a and FIG. 4b also show a respective actual body reflection term ($c_0 * \underline{b}^*$), also referred to as physiologic reflection component 100. The term $c_2 \underline{s}$, or, the disturbing reflection portion 102 is considered parallel to the luminance index element 94 since specular reflection basically mirrors the incident light. Thus, the respective signal component 102 is at least partially indicative of a light source characteristic, e.g., indicated by the luminance index element 94.

The signal space 88 further comprises a dichromatic plane 96 which is basically formed by the disturbing reflection component 102 and the basic reflection portion 104, or, in other words, the dichromatic plane 96 is spanned by the vectors $\underline{s}$ and $\underline{b}$. In the following, $\underline{b}$, $\underline{h}$ and $\underline{s}$ can be considered unit vectors indicating orientation and direction, while $c_0$, $c_1$ and $c_2$ can be considered respective coefficients indicating length. When neglecting the indicative reflection portion 106 (or, $c_1 \underline{h}$) the remaining signal components 102, 104 can be considered to lie in the dichromatic plane 96.

Further, when also referring to FIG. 2, the physiologic reflection component 100 can be traced back to the body reflection 80 (incorporating the desired signals) while the disturbing reflection component 102 can be traced back to the interface reflection 76.

In the following section, an approach to standard (obtrusive) photoplethysmography under consideration of the extended dichromatic reflection model outlined above is provided. For standard PPG, the heart beat signal is commonly measured in an enclosure (e.g., an pulse-oximeter), wherein distortion due to specular reflectance does not play a role. Consequently, the specular reflectance component $c_2 \underline{s}$ in the (extended) dichromatic reflection model can be estimated to basically equal zero. Accordingly, the characteristic signal $\underline{p}$ obtained through the sensor means can be described by a linear combination of the body reflection vector $\underline{b}$ and the heart beat vector $h$ (refer equation (7) with $c_2 = 0$):

$$\underline{p}(n) = c_0(n)\underline{b} + c_1(n)\underline{h},$$

wherein the vector $\underline{p}$ can contain respective red and infrared signals (also referred to as main components in the following), and where n corresponds to time. Or more explicitly, $$\begin{bmatrix} v_r(n) \\ v_{ir}(n) \end{bmatrix} = \underline{p}(n) = c_0(n)\underline{b} + c_1(n)\underline{h}.$$

In this context, it should be understood that also RGB signals can be utilized as main components of the vector $\underline{p}$. For instance, red and green signals can be analyzed so as to detect the desired vital signal of interest. When further normalizing the term under consideration of $\overline{c}_1 = 0$ (basically, the heart beat signal exhibits a zero mean), a mean vector $\overline{\underline{p}}$ equals $$\overline{\underline{p}} = \overline{c}_0 \underline{b}.$$

Furthermore, the red and infrared signals can be normalized for varying luminance intensity and for skin color differences by dividing the respective signals by their mean values so as to link this expression with the equations (2) and (3). Normalization basically comprises a division by the mean intensity $\overline{c}_0$ of the illumination and by the body reflection vector $\underline{b}$. The body reflection vector $\underline{b}$ can be considered the result of the (mean) reflectance of the red and infrared light by the object's skin. This division results in the normalized vector $\underline{p}_n$:

$$\begin{aligned} \underline{p}_n(n) &= \frac{1}{\overline{c}_0} B^{-1} \underline{p}(n) \\ &= \frac{c_0(n)}{\overline{c}_0} \underline{1} + \frac{c_1(n)}{\overline{c}_0} B^{-1} \underline{h} \\ &= \frac{c_0(n)}{\overline{c}_0} \underline{1} + \frac{c_1(n)}{\overline{c}_0} \|B^{-1}\underline{h}\| \underline{h}_n, \end{aligned} \quad (8)$$

wherein $\|\cdot\|$ denotes the ordinary $l_2$-norm, wherein the diagonal matrix B has the body reflection vector $\underline{b}$ on the diagonal, wherein the vector $\underline{1}$ is the vector containing the values one and the vector $\underline{h}_n$ corresponds to the normalized heart beat vector which is independent of the skin type:

$$\underline{h}_n = \frac{1}{\|B^{-1}\underline{h}\|} B^{-1} \underline{h}. \quad (9)$$

It should be understood that basically the skin color becomes gray due to this normalization. In other words, the body reflection vector equals the vector $\underline{1}$, refer equation (8). In the alternative, one could start with an estimate of the body reflection vector $\underline{b}$ and the normalized heart beat vector $h_n$, from which the heart beat vector $h$ can be derived as follows, for instance in the RGB signal space:

$$\underline{h} = \frac{B\underline{h}_n}{\|B\underline{h}_n\|}. \quad (10)$$

This expression is based on equation (9) in combination with a normalization to unit length.

In the following section, the presented approach is extended so as to further cover remote (unobtrusive) photoplethysmography. For remote PPG, specular reflectance has to be considered. According to the extended dichromatic reflection model outlined above, the characteristic signal $\underline{p}(n)$ obtained from the remote sensor means can be described as a linear combination of the body reflection vector $\underline{b}$, the heart beat vector $h$ and the interface reflection vector $\underline{s}$ (see also equation (7)):

$$\underline{p}(n) = c_0(n)\underline{b} + c_1(n)\underline{h} + c_2(n)\underline{s}. \quad (11)$$

To estimate the heart rate of an object of interest, the time-dependent signal $c_1$ has to be analyzed, similar to the case of standard PPG. In order to analyze this signal, it has to be separated from the two other signals $c_o$ and $c_2$. Moreover, to reduce the effect of the (changing) intensity of the illumination, the signal $c_1$ can be divided by (or, normalized for) the intensity $c_o$ or the mean intensity $\overline{c}_o$. However, this can be considered an optional step. Especially when only small intensity changes are expected, the intensity normalization can be omitted. Another exemplary normalization step can comprise a division of the resulting signal by the body reflection vector $\underline{b}$.

In the following section, approaches to an algebraic separation of the signals $c_0$, $c_1$ and $c_2$ are presented. Equation (11) can be rewritten in a matrix-vector product:

$$\underline{p}(n) = T\underline{c}(n), \text{ with } T = [\underline{b}\ \underline{h}\ \underline{s}] \text{ and } \underline{c}(n) = \begin{bmatrix} c_0(n) \\ c_1(n) \\ c_2(n) \end{bmatrix},$$

wherein $c_o$ can be also referred to as basic reflection coefficient, $c_1$ can be also referred to as indicative reflection coefficient, and $c_2$ can be also referred to as disturbing reflection coefficient.

Considering this expression, it may be concluded that the signals $c_0$, $c_1$ and $c_2$ can, at least in principle, be obtained by multiplying this expression with the inverse matrix $T^{-1}$ on both sides:

$$\underline{c}(n) = T^{-1}\underline{p}(n). \quad (12)$$

Equation (12) can be considered a linear algebraic equation built up under consideration of a defined component representation. Consequently, the vital signal of interest $u(n)$, e.g., the heart beat signal, becomes $$u(n) = \frac{c_1(n)}{c_0(n)}, u(n) = \frac{c_1(n)}{\overline{c}_0}, \text{ or simply } u(n) = c_1(n). \quad (13)$$

Furthermore, the signal u can be filtered by a band-pass filter to filter out frequency content outside the frequency range of interest.

In order to compute the inverse matrix $T^{-1}$, the body reflection vector $\underline{b}$ and the specular reflection vector $\underline{s}$ have to be estimated. Furthermore, as shown above, the heart beat vector h may be derived from the body reflection vector $\underline{b}$, refer equation (10). For the specular reflection term, it can be considered that for materials with high oil or water content, like skin, the light reflected from the material's surface basically appears to exhibit the same color as the illuminant. As a first approximation, it can be fairly assumed that the illumination is white (e.g., RGB=1,1,1). That is, the specular reflection vector $\underline{s}$ can be considered equal to the one vector$\underline{1}$. Furthermore, the body reflection vector $\underline{b}$ can be considered equivalent to the mean red, mean green and mean blue of the skin pixels of the object of interest in an initial frame of a captured sequence of frames. Accordingly, a normalization to unit length can be applied:

$$T = [\underline{b}\ h\ \underline{1}].$$

Hence, the signal of interest u can be obtained by applying equations (12) and (13).

Instead of using equation (10), it can be also envisaged to use the vector orthogonal to the body reflection vector $\underline{b}$ and interface vector $\underline{s} = \underline{1}$ as the indicative (heart beat) vector h. This approach is based on the insight that according to an advantageous assumption the indicative (heart beat) vector h is independent from $\underline{s}$ and $\underline{b}$ and therefore basically points out of the dichromatic plane, see reference sign 96 in FIG. 4a. Consequently, varying illumination conditions do not significantly affect the indicative (heart beat) vector h.

In the following section, the model and approaches outlined above are expanded to logarithmic signal spaces. For instance, a log RGB color space can be utilized. When deriving equation (3), also the logarithm operator was utilized. When taking the logarithm, a prior signal filtering, e.g. band pass filtering, has to be avoided so as to prevent applying the logarithm operator to signal samples smaller than or equal to zero. Thus, the filter step can be carried out preferably after applying the logarithm operator. Consequently, for remote PPG monitoring, the mean red, green and blue values (also referred to as main components) of the characteristic signal $\underline{p}(n)$ are still affected by specular reflection. Hence, a mean specular reflection value is still present in the mean red, green and blue values.

This case can be handled when assuming a ratio between expected specular reflection and the body reflection, e.g., a ratio between the coefficients $c_2$ and $c_0$ which will be presented in the following.

The logarithm operator can be applied (element wise) to the expression presented in equation (11):

$$\log \underline{p}(n) = \log [c_0(n)\underline{b} + c_1(n)h + c_2(n)\underline{s}].$$

A first assumption can consider that the amount of specular reflection equals zero, i.e. $c_2(n)=0$ for all n. The following terms arise accordingly $$\log \underline{p}(n) = \log[c_0(n)\underline{b} + c_1(n)\underline{h}]$$

$$= \log \underline{b} + \log[c_0(n)\underline{1} + c_1(n)B^{-1}\underline{h}]$$

$$= \log \underline{b} + \log[c_0(n)]\underline{1} + \log\left[\underline{1} + \frac{c_1(n)}{c_0(n)}B^{-1}\underline{h}\right]$$

$$\approx \log \underline{b} + \log[c_0(n)]\underline{1} + \frac{c_1(n)}{c_0(n)}B^{-1}\underline{h}$$

$$= \log \underline{b} + \log[c_0(n)]\underline{1} + \frac{c_1(n)}{c_0(n)}\|B^{-1}\underline{h}\|\underline{h}_n,$$

wherein the elements of the diagonal matrix B are considered equal to the elements of the body reflection vector $\underline{b}$. From this expression it can be concluded that for an ideal case without specular reflection the RGB space spanned by a body reflection vector $\underline{b}$ and a heart beat vector h can be transformed into a log RGB space spanned by an intensity vector $\underline{1}$ and a normalized heart beat vector $\underline{h}_n$.

For situations wherein the amount of specular reflection deviates from zero, further cases can be plotted. In a first case, the amount of specular reflection is considered relatively small when compared to the body reflection, i.e. $c_0(n) \gg c_2(n)$. Then the following terms can be derived:

$$\log \underline{p}(n) = \log[c_0(n)\underline{b} + c_1(n)\underline{h} + c_2(n)\underline{s}]$$

$$= \log \underline{b} + \log[c_0(n)]\underline{1} + \log\left[\underline{1} + \frac{c_1(n)}{c_0(n)}B^{-1}\underline{h} + \frac{c_2(n)}{c_0(n)}B^{-1}\underline{s}\right]$$

$$\approx \log \underline{b} + \log[c_0(n)]\underline{1} + \frac{c_1(n)}{c_0(n)}\|B^{-1}\underline{h}\|\underline{h}_n + \frac{c_2(n)}{c_0(n)}B^{-1}\underline{s}.$$

From this expression it can be concluded that the RGB space spanned by a body reflection vector $\underline{b}$, a heart beat vector h, and an interface reflection vector $\underline{s}$ can be transformed into a log RGB space spanned by a normalized body reflection vector $\underline{1}$, a normalized heart beat vector $\underline{h}_n$ and a modified interface reflection vector $B^{-1}\underline{s}$. That is, a heart beat signal can be extracted in a similar way as described above.

In another case, it can be assumed that the amount of specular reflection is relatively large compared to the amount of body reflection, i.e. $c_0(n) \ll c_2(n)$. Consequently, the following terms can be derived $$\log \underline{p}(n) = \log[c_0(n)\underline{b} + c_1(n)\underline{h} + c_2(n)\underline{s}]$$

$$= \log \underline{s} + \log[c_2(n)]\underline{1} + \log\left[\underline{1} + \frac{c_1(n)}{c_2(n)}S^{-1}\underline{h} + \frac{c_0(n)}{c_2(n)}S^{-1}\underline{b}\right]$$

$$\approx \log \underline{s} + \log[c_2(n)]\underline{1} + \frac{c_1(n)}{c_2(n)}S^{-1}\underline{h} + \frac{c_0(n)}{c_2(n)}S^{-1}\underline{b},$$

wherein the elements of the diagonal matrix S are equal to the elements of the interface reflection vector $\underline{s}$. This expression allows a conclusion according to which the RGB space which is spanned by a body reflection vector $\underline{b}$, a heart beat vector h, and an interface reflection vector $\underline{s}$ can be transformed into a log RGB space spanned by an interface reflection vector $\underline{1}$, a modified heart beat vector $S^{-1}h$ and a modified body reflection vector $S^{-1}\underline{b}$. As a result, instead of having a known heart beat vector $h_n$, a heart beat vector can be obtained that depends on the color of the illuminant. Moreover, the amplitude of the heart beat signal depends on the amount of specular reflection $c_2$ instead of the amount of body reflection $c_0$. Consequently, in this case the log RGB space can be considered less suitable to extract the heart beat signal, since the amount of specular reflection is relatively large.

In an even further case it can be assumed that basically the amount of specular reflection is similar to the amount of body reflection, i.e. $c_0(n) \approx c_2(n)$. As a result, the following term can be derived:

$$\log \underline{p}(n) = \log[c_0(n)\underline{b} + c_1(n)\underline{h} + c_2(n)\underline{s}]$$

$$= \log \underline{g} + \log[c_0(n)]\underline{1} + \log\left[\underline{1} + \frac{c_1(n)}{c_0(n)}G^{-1}\underline{h}\right]$$

$$\approx \log \underline{g} + \log[c_0(n)]\underline{1} + \frac{c_1(n)}{c_0(n)}G^{-1}\underline{h},$$

wherein $\underline{g}=\underline{b}+\underline{s}$, and wherein the elements of the diagonal matrix G are equal to the elements of the vector $\underline{g}$. Based on this expression, it can be concluded that the RGB space which is spanned by a body reflection vector $\underline{b}$, a heart beat vector h, and an interface reflection vector $\underline{s}$ can be transformed into a log RGB space spanned by a vector $\underline{1}$, and a modified heart beat vector $G^{-1}h$.

To summarize the above cases, it can be can concluded that for an increasing amount of specular reflection the normalized heart beat vector $h_n$ is transformed into the modified heart beat vector $S^{-1}h$ via a so-called intermediate heart beat vector $G^{-1}h$.

However, in many cases the amount of specular reflection can be expected to be relatively small, and, consequently, the heart beat vector merely changes slightly. In case, however, the expected amount of specular reflection is large, it can be considered to reduce the specular reflection by first projecting the RGB space onto a plane orthogonal to the interface reflection vector $\underline{s}$, before applying the logarithm operator. In this case, so as to reduce the specular reflection properly, it would be advantageous to determine the illuminant color. However, if the illuminant color is known, for example for the most common case involving basically white illuminant, this approach is applicable.

Figure 5:
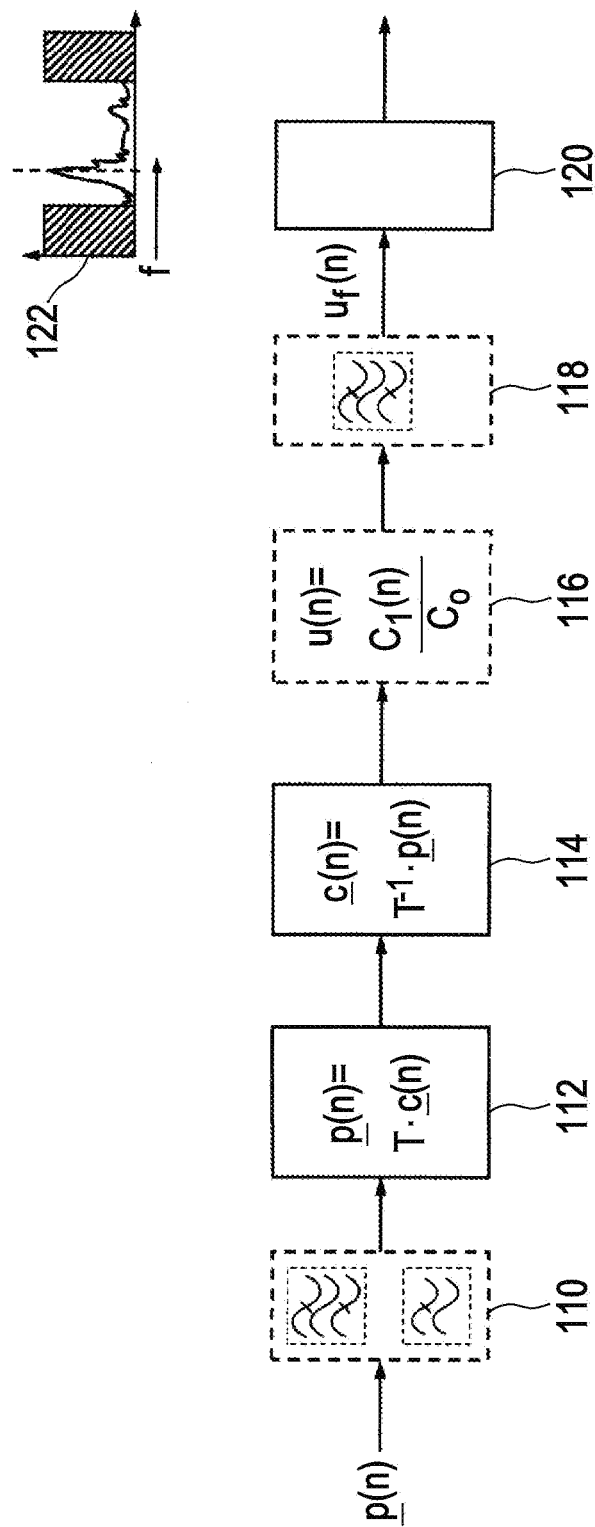
FIG. 5 shows a schematic illustration of a system comprising signal conversion and signal processing.

In the following section a general framework of several examples utilizing the approaches outlined above is described. In this connection, FIG. 5 is referred to. FIG. 5 shows a simplified block diagram of a system or method for extracting information. Basically, the system is arranged for processing a characteristic signal $\underline{p}(n)$ comprising several steps that have been introduced above and can be utilized by the examples presented in the following. Needless to say, some of the steps can be considered optional which is indicated by dashed lines. In a first step 110 the characteristic input signal $\underline{p}(n)$ is filtered. Filtering can comprise band pass filtering, low pass filtering, and high pass filtering. Further filter characteristics can be applied as well. The (input) filtering can be directed to attenuate non-indicative frequency portions and to enhance potentially indicative frequency portions of the characteristic signal $\underline{p}(n)$.

A further step 112 may follow comprising building up and/or establishing a linear algebraic equation under consideration of a substantially linear algebraic signal composition model. Basically, step 112 can make use or the signal representation model shown in equation (11): $\underline{p}(n)=c_0(n) \underline{b}+c_1(n) \underline{h}+c_2(n)\underline{s}$. In a vector-matrix representation, this equation can be represented by the term $\underline{p}(n)=T\underline{c}(n)$.

In a subsequent step 114 the equation built up in step 112 can be rearranged so as to arrive at a term similar to equation (12). Furthermore, equation (12) can be at least partially solved in step 114 so as to obtain an indicative signal representation, for instance, $\underline{c}(n)$, or, at least, $c_1(n)$.

In a further, optional step 116, the signal derived through step 114 can be normalized for intensity by dividing it, for instance, by the coefficient $c_o(n)$ or the mean coefficient $\bar{c}_o$. Consequently, a signal u(n) can be obtained which is considered highly indicative of the desired signal of interest. It should be noted that for some applications, the coefficient $c_o(n)$ (or, $\bar{c}_o$) should not undergo a filtering step prior to the optional step 116 so as to avoid undesired conversions thereof. Probably, these conversions can further adversely affect the ratio to be calculated in step 116.

In another optional step 118 the signal, e.g. $c_1(n)$, or u(n) can be filtered so as to further enhance signal quality. Post-filtering as well as pre-filtering can be directed to several operational issues and constraints. Consequently, in step 118 a filtered indicative signal $u_f(n)$ can be derived.

Furthermore, a subsequent step 120 may follow for extracting the vital signal of interest, e.g. the heart rate, from the filtered indicative signal $u_f(n)$. For instance, the extraction can be directed to detect frequency peaks of the time-based signal $u_f(n)$. In this connection, reference sign 122 indicates a respective frequency response diagram having suppressed (filtered out) bands and a passed band in which a clear frequency peak is detected. For instance, the frequency peak can exhibit the heart beat of an observed object of interest.

In line with the aforesaid description, the general framework relies on a matrix T, for instance, a fixed matrix T. This approach can be traced back to the equations (12) and (13). Accordingly, the mean red, mean green and mean blue values in the vector $\underline{p}$ are transformed to the vector $\underline{c}$ by means of a matrix multiplication. Then, as an optional measure, the heart beat signal $c_1$ can be compensated for the intensity, resulting in the heart beat signal u. For further enhancing this heart beat signal, the heart beat signal u can be filtered by a band pass filter. Typically, indicating a frequency range of interest, for instance, a pass band including a range of about 35 beats per minute (BPM) to about 210 BPM can be utilized. Basically, the following examples rely on a vector space based point of view.

However, in particular, for some applications, especially when merely the heart beat is the signal of interest, it is not necessary to compute the whole inverse matrix $T^{-1}$ of the matrix T. For instance, an inner product $\langle \underline{p}(n), h. \rangle$, wherein h is considered orthogonal to the dichromatic plane, can be considered highly indicative of the desired (heart beat) signal.

In a first example, the body reflection vector $\underline{b}$ can be estimated once, for example by computing the mean red, mean green and mean blue values of the skin pixels in the first frame of a sequence of frames. Furthermore, it can be fairly assumed that the color of the illuminant is white, i.e. the interface reflection vector $\underline{s}=\underline{1}$. Consequently, the heart beat vector h can follow directly from the body reflection vector, refer equation (10). The transformation matrix T now equals $$T=[\underline{b}\ h\ \underline{1}],$$

and, accordingly, the equations (12) and (13) can be used to compute the heart beat signal u. Additionally, this heart beat signal can be filtered by a band-pass filter to filter out frequency content outside the frequency range of interest.

Alternatively, the heart beat vector h can be considered equal to the vector orthogonal to the dichromatic plane, i.e. $h=\underline{b}\times\underline{1}$. This approach can be preferred in case the illuminant spectrum is unknown and, accordingly, the normalized heart beat vector $h_n$ cannot be determined. Hence, given the three vectors, the transformation matrix T can be constructed:

$$T=[\underline{b}\ \underline{b}\times\underline{1}\ \underline{1}],$$

and, again, equations (12) and (13) can be utilized to compute the heart beat signal u.

In a second example, modifying the first example, the characteristic signal $\underline{p}$ can be normalized by dividing it by the body reflection vector $\underline{b}$ (represented by the diagonal matrix B)

$$\underline{p}_n = B^{-1} \underline{p}(n),$$

wherein preferably the normalization is carried out instantaneously. The normalization relies on the body reflection vector $\underline{b}$ which is independent of the heart beat vector h and basically constant, and therefore does not contain a heart beat signal.

Due to the normalization, the matrix T is slightly modified: the normalized body reflection vector is now represent by the $\underline{1}$ vector, the heart beat vector becomes the normalized heart beat vector $h_n$, and the interface (specular) reflection vector becomes the normalized interface reflection vector $B^{-1}\underline{s}$. Consequently, these normalized vectors can be used to construct the matrix T:

$$T=B^{-1}[\underline{b}h\underline{1}]=[\underline{1}\ h_n\ B^{-1}\underline{s}],$$

and, again, equations (12) and (13) can be considered to compute the heart beat signal u. It should be noted that this example can be considered basically equivalent to the previous example, since there is primarily a body reflection indicative matrix B involved.

A third example is based on the insight that due to the specular reflection the body reflection vector can be considered approximately the same for various skin types under basically white light. In general, this assumption holds up to a maximal deviation of about 2.5 degrees. Furthermore, a vector $\underline{b}_n$ can be defined which can be considered the mean body reflection vector for all skin types under white light. Accordingly, a corresponding diagonal matrix $B_n$ with $\underline{b}_n$ as diagonal can be established. Hence, an approximation of the interface reflection $\underline{s}$ can be derived:

$$\underline{s}=B_n^{-1}\underline{b},$$

wherein $\underline{b}$ can be considered the approximated body reflection vector. Consequently, the heart beat vector h now equals $Bh_n$ and the matrix T can be constructed as follows:

$$T=[\underline{b}\ Bh_n\ B_n^{-1}\underline{b}],$$

and, again, equations (12) and (13) can be used to compute the heart beat signal u. Alternatively, h can equal the vector orthogonal to the body reflection vector $\underline{b}$ and the interface reflection vector $B^{-1}\underline{b}$:

$$T=[\underline{b}\ \underline{b}\times(B_n^{-1}\underline{b})B_n^{-1}\underline{b}].$$

In case the color of the illumination is expected to (slowly) change in time, it can be considered to also estimate and filter the body reflection vector continuously. The filtering can be carried out utilizing a low pass filter, refer the filtering step 110 in FIG. 5, to enhance the heart beat signal. Accordingly, the matrices T and $T^{-1}$ can be modified and adapted continuously.

In a fourth example, the logarithm operator is applied to the characteristic signal $\underline{p}$. As indicated above, taking the logarithm of zero values or even small numbers should be avoided. Basically, a matrix T can be constructed, for instance, according to one of the previous examples. Accordingly, the inverse matrix $T^{-1}$ can be applied to the signal p aiming at the vector $\underline{c}$:

$$\underline{c}(n)=T^{-1}\underline{p}(n).$$

According to this example, the third row of this obtained vector $\underline{c}$ can be discarded since it basically corresponds to the specular reflection. In other words, a 2×3 matrix T can be defined comprising rows that correspond to the first two rows of $T^{-1}$ and this matrix can be applied to the signal p:

$$\hat{\underline{c}}(n) = \begin{bmatrix} c_0(n) \\ c_1(n) \end{bmatrix} = \hat{T}\underline{p}(n).$$

The signal $c_0$ represents the intensity signal with a mean $\bar{c}_0$, while the signal $c_1$ represents the heart beat signal with a mean close to zero. Therefore, to be able to apply the logarithm operator to this signal $\hat{\underline{c}}$, a basis change can be carried out by applying the matrix U to the term:

$$\underline{y}(n)=U\hat{T}\underline{p}(n),$$

wherein $$U = \begin{bmatrix} \frac{1}{2}\sqrt{2} & \frac{1}{2}\sqrt{2} \\ \frac{1}{2}\sqrt{2} & -\frac{1}{2}\sqrt{2} \end{bmatrix}.$$

The goal of this transformation is to make sure that the heart beat signal has a mean significantly larger than zero. This matrix U can be chosen in such a way that basically both signals have a mean of approximately $\frac{1}{2}\sqrt{2\bar{c}_0}$. Of course, other matrices apart from the exemplary matrix U can be envisaged.

Subsequently, the logarithm operator can be applied on a element-per-element basis to the vector y. Furthermore, the inverse matrix $U^{-1}$ can be utilized so as to obtain the vector $\underline{z}$:

$$\underline{z}(n) = \begin{bmatrix} z_0(n) \\ z_1(n) \end{bmatrix} = U^{-1}\log[\underline{y}(n)].$$

Consequently, the signal $z_1$ can correspond to the heart beat signal.

In a fifth example, attention is directed to the detection of a so called dynamic heart beat axis. The dynamic heart beat axis can be applied in case the characteristic signals are widely affected by undesired object motion. In this context, it would be advantageous to utilize a reasonably well approximated heart beat axis h.

Initially, the matrix T can be constructed in accordance with the third example, wherein a heart beat vector orthogonal to the dichromatic plane is considered. Subsequently, the mean red, mean green, and mean blue values can be buffered for a short amount of time, e.g., about 10 to 15 seconds. Further, the vector $\underline{p} \in R^{3 \times N}$ can be introduced for containing these mean values, wherein N also corresponds to 10 to 15 seconds. Subsequently, the inverse matrix $T^{-1}$ can be applied to this vector so as to obtain the vector $\underline{c}$:

$$\underline{c}(n) = T^{-1}\underline{p}(n), \text{ with } n=0 \ldots N-1.$$

Furthermore, each row of the signals in $\underline{c}$ can be band pass filtered so as to attenuate content outside the frequency range of interest. The band pass filtered signal $c_1$ now already can contain a potentially indicative heart beat signal, assumed that the motion of the individual is not too severe. For instance, this can be verified by transforming the signal $c_1$ to the Fourier domain and detecting the signal-to-noise-ratio by computing the largest peak over the second largest peak ratio. If this ratio is above a certain threshold, the band pass filtered signal $c_1$ can be considered clean enough to be used as a template. The heart beat amplitudes $a_0$ and $a_2$ in the band pass filtered signals $c_0$ and $c_2$ can now be computed by $$a_0 = \frac{\langle c_0, c_1 \rangle}{\|c_1\|^2}, \text{ and } a_2 = \frac{\langle c_2, c_1 \rangle}{\|c_1\|^2},$$

wherein $\langle \ldots, \ldots \rangle$ corresponds to an inner product. Basically, the following terms are computed $$a_0 = \underset{a \in R}{\operatorname{argmin}} \|c_1 - ac_0\|^2, \text{ and } a_2 = \underset{a \in R}{\operatorname{argmin}} \|c_2 - ac_0\|^2.$$

Furthermore, it should be noted that $a_1 = 1$ since $$a_1 = \frac{\langle c_1, c_1 \rangle}{\|c_1\|^2} = 1.$$

Consequently, this example results in the heart beat vector $\tilde{h}$ $$\underline{\tilde{h}} = \begin{bmatrix} a_0 \\ 1 \\ a_2 \end{bmatrix},$$

and, when also referring the RGB signal space, the heat beat vector h becomes $$h = T\tilde{h}.$$

However, alternatively, it can be further envisaged to detect relevant signal frequency peaks upon applying the Fourier transformation to the (band pass filtered) red, green and blue signals (also referred to as main components in the above).

Basically, referring to all examples and embodiments provided in the above sections, it should be understood that the construction of the matrix T and the at least partial calculation of the inverse matrix $T^{-1}$ so as to obtain the coefficients $c_0$, $c_1$ and $c_2$, in the alternative, can be complemented or replaced a by step-wise transformation utilizing geometrical associations of the characteristic signal $\underline{p}(n)$ and further components of the signal space. In other words, matrix operations can be readily replaced by step-wise vector operations.

By way of example, the present invention can be applied in the field of health care, e.g. unobtrusive remote patient monitoring, general surveillances, security monitoring and so-called lifestyle applications, such as fitness equipment, or the like. Applications may include monitoring of oxygen saturation (pulse oxymetry), heart rate, respiration rate, blood pressure, cardiac output, changes of blood perfusion, assessment of autonomic functions and detection of peripheral vascular diseases.

Needles to say, in an embodiment of a method in accordance with the invention several of the steps provided can be carried out in changed order, or even concurrently. Further, some of the steps could be skipped as well without departing from the scope of the invention. This applies in particular to several alternative signal processing steps.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the words "comprising" and "including" do not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Device for extracting information from detected characteristic signals, comprising:

an interface (28) for receiving a data stream (26) derivable from electromagnetic radiation (14) reflected by an object (12), the data stream (14) comprising a continuous or discrete time-based characteristic signal (p; 98), the characteristic signal (p; 98) comprising at least two main components (92a, 92b, 92c) associated with a signal space (88), the signal space (88) comprising complementary channels (90a, 90b, 90c) for representing the characteristic signal (p; 98), the main components (92a, 92b, 92c) of the characteristic signal (p; 98) being related to respective complementary channels (90a, 90b, 90c) of the signal space (88), a converter means (36) for mapping the characteristic signal (p; 98) to a defined component representation (b, h, s, c; T, c) under consideration of a substantially linear algebraic signal composition model so as to specify a linear algebraic equation, the characteristic signal (p; 98) being at least substantially composed of a physiologic reflection component (100) and a disturbing reflection component (102), wherein the physiologic reflection component (100) comprises a basic reflection portion (104) attributable to basic physiologic properties of the object (12) to be observed and an indicative reflection portion (106) attributable to at least one at least partially periodic vital signal (20), wherein the basic reflection portion (104) comprises a basic reflection index element (b̲) and a basic reflection coefficient ($c_0$), wherein the indicative reflection portion (106) comprises an indicative reflection index element (h̲) and a time-dependent indicative reflection coefficient ($c_1$), the indicative reflection coefficient ($c_1$) being highly indicative of the at least one at least partially periodic vital signal (20) of interest, wherein the disturbing reflection component (102) comprises a disturbing reflection index element (s̲) and a disturbing reflection coefficient ($c_2$), a processing means (40) for at least partially solving the linear algebraic equation under consideration of an at least approximate estimation of the orientation of the basic reflection index element (b̲), the indicative reflection index element (h̲) and the disturbing reflection index element (s̲) so as to derive an expression highly indicative of the at least one at least partially periodic vital signal (20), the highly indicative expression at least comprising the indicative reflection coefficient ($c_1$).

2. Device as claimed in claim 1, wherein the at least one at least partially periodic vital signal (20) is selected from the group consisting of heart rate, heart beat, respiration rate, heart rate variability, Traube-Hering-Mayer waves, and oxygen saturation, and wherein the signal space (88) is an additive or subtractive color signal space, wherein the at least two main components (92a, 92b, 92c) represent respective distinct color components indicated by the complementary channels (90a, 90b, 90c), wherein the complementary channels (90a, 90b, 90c) are related to defined spectral portions.

3. Device as claimed in claim 1, further comprising an extractor means (52) for extracting the vital signal (20) from the computed highly indicative expression, preferably the vital signal is extracted under consideration of the indicative reflection coefficient ($c_1$) or of a ratio of the indicative reflection coefficient ($c_1$) and the basic reflection coefficient ($c_0$).

4. Device as claimed in claim 1, wherein the basic reflection portion (104) is at least substantially indicative of a mean tissue color the object of interest (12) exhibits, wherein the indicative reflection portion (106) is at least substantially indicative of an at least partially periodic pulsation of the tissue color of the object of interest (12), and wherein the disturbing reflection component (102) is at least substantially indicative of disturbing specular reflection.

5. Device as claimed in claim 1, wherein the estimated indicative reflection index element (h) is obtained under consideration of an expression comprising the estimation of the basic reflection index element (b̲) and a normalized expression of a predetermined exemplary indicative reflection index element ($h_n$).

6. Device as claimed in claim 1, wherein the estimated indicative reflection index element (h) is considered orthogonal to a signal plane spanned by the basic reflection index element (b̲) and the disturbing reflection index element (s̲), and wherein the estimated disturbing reflection index element (s̲) is at least substantially aligned with a luminance index element (94) being indicative of characteristics of an electromagnetic radiation source (16) affecting the object of interest (12).

7. Device as claimed in claim 1, wherein the estimated basic reflection index element (b̲) is derived from agglomerated main components (92a, 92b, 92c) of the characteristic signal (p̲; 98) of an indicative area (22) of the object of interest (12), and wherein the estimated disturbing reflection index element (s̲) is at least substantially aligned with a luminance index element (94) being indicative of characteristics of an electromagnetic radiation source (16) affecting the object of interest (12), preferably the device is further adapted to apply an initial determination of the basic reflection index element (b̲) when observing the object of interest (12).

8. Device as claimed in claim 7, wherein the estimated indicative reflection index element (h) is considered at least substantially orthogonal to the basic reflection index element (b̲) and at least substantially orthogonal to the disturbing reflection index element (s̲).

9. Device as claimed in claim 1, wherein a logarithmic signal representation is applied to the defined component representation (b̲, h, s̲, c̲; T̲, c̲), preferably an assumed ratio between the basic reflection coefficient ($c_0$) and the disturbing reflection coefficient ($c_2$) is taken into consideration for the determination of the indicative reflection coefficient ($c_1$).

10. Device as claimed in claim 9, wherein a basis change is applied to the defined component representation (b̲, h, s̲, c̲; T̲, c̲) so as to ensure that a mean value of the indicative reflection coefficient ($c_1$) is greater than zero, and wherein the vital signal (20) can be derived from a transformed representation ($z_1$) of the indicative reflection coefficient ($c_1$).

11. Device as claimed in claim 1, further comprising a normalization of the characteristic signal (p̲; 98) under consideration of the basic reflection index element (b̲).

12. Device as claimed in claim 1, wherein the disturbing reflection index element (s̲) is obtained under consideration of an expression comprising a predetermined normalized value of the basic reflection index element (b̲) obtained under consideration of an assumed standard orientation of a luminance index element (94) being indicative of characteristics of an electromagnetic radiation source (16) affecting the object of interest (12).

13. Device as claimed in claim 1, further comprising a buffer means for buffering the characteristic signal (p̲; 98) and a resulting representation (c̲) of the basic reflection coefficient ($c_0$), the indicative reflection coefficient ($c_1$) and the disturbing reflection coefficient ($c_2$) for a defined period, wherein the processing means (40) is further adapted to apply a Fourier transformation to the buffered indicative reflection coefficient ($c_1$) so as to determine dominant frequency components thereof, wherein the basic reflection coefficient ($c_0$), the indicative reflection coefficient ($c_1$) and the disturbing reflection coefficient ($c_2$) are transferred to a transformed signal representation ($a_0$, $a_1$, $a_2$) comprising inner products of respective coefficients ($c_0$, $c_1$, $c_2$), wherein the indicative reflection index element (h̲) is determined under consideration of the transformed signal representation ($a_0$, $a_1$, $a_2$).

14. Method for extracting information from detected characteristic signals, comprising the steps:

receiving a data stream (26) derivable from electromagnetic radiation (14) reflected by an object (12), the data stream (14) comprising a continuous or discrete time-based characteristic signal (p̲; 98), the characteristic signal (p̲; 98) comprising at least two main components (92a, 92b, 92c) associated with a signal space (88), the signal space (88) comprising complementary channels (90a, 90b, 90c) for representing the characteristic signal (p̲; 98), the main components (92a, 92b, 92c) of the characteristic signal (p̲; 98) being related to respective complementary channels (90a, 90b, 90c) of the signal space (88), mapping the characteristic signal (p̲; 98) to a defined component representation (b̲, h, s̲, c̲; T̲, c̲) under consideration of a substantially linear algebraic signal composition model so as to specify a linear algebraic equation, the characteristic signal (p; 98) being at least substantially composed of a physiologic reflection component (100) and a disturbing reflection component (102), wherein the physiologic reflection component (100) comprises a basic reflection portion (104) attributable to basic physiologic properties of the object (12) to be observed and an indicative reflection portion (106) attributable to at least one at least partially periodic vital signal (20), wherein the basic reflection portion (104) comprises a basic reflection index element (b) and a basic reflection coefficient ($c_0$), wherein the indicative reflection portion (106) comprises an indicative reflection index element (h) and a time-dependent indicative reflection coefficient ($c_1$), the indicative reflection coefficient ($c_1$) being highly indicative of the at least one at least partially periodic vital signal (20) of interest, wherein the disturbing reflection component (102) comprises a disturbing reflection index element (s) and a disturbing reflection coefficient ($c_2$), at least partially solving the linear algebraic equation under consideration of an at least approximate estimation of the orientation of the basic reflection index element (b), the indicative reflection index element (h) and the disturbing reflection index element (s) so as to derive an expression highly indicative of the at least one at least partially periodic vital signal (20), the highly indicative expression at least comprising the indicative reflection coefficient ($c_1$).

15. A non-transitory computer-readable medium comprising computer executable instructions that when executed by a computer cause the computer to carry out the steps of the method as claimed in claim 14.

* * * * *